March 19, 1974 S. McGREDY Plant Pat. 3,524
ROSE PLANT
Filed Sept. 25, 1972
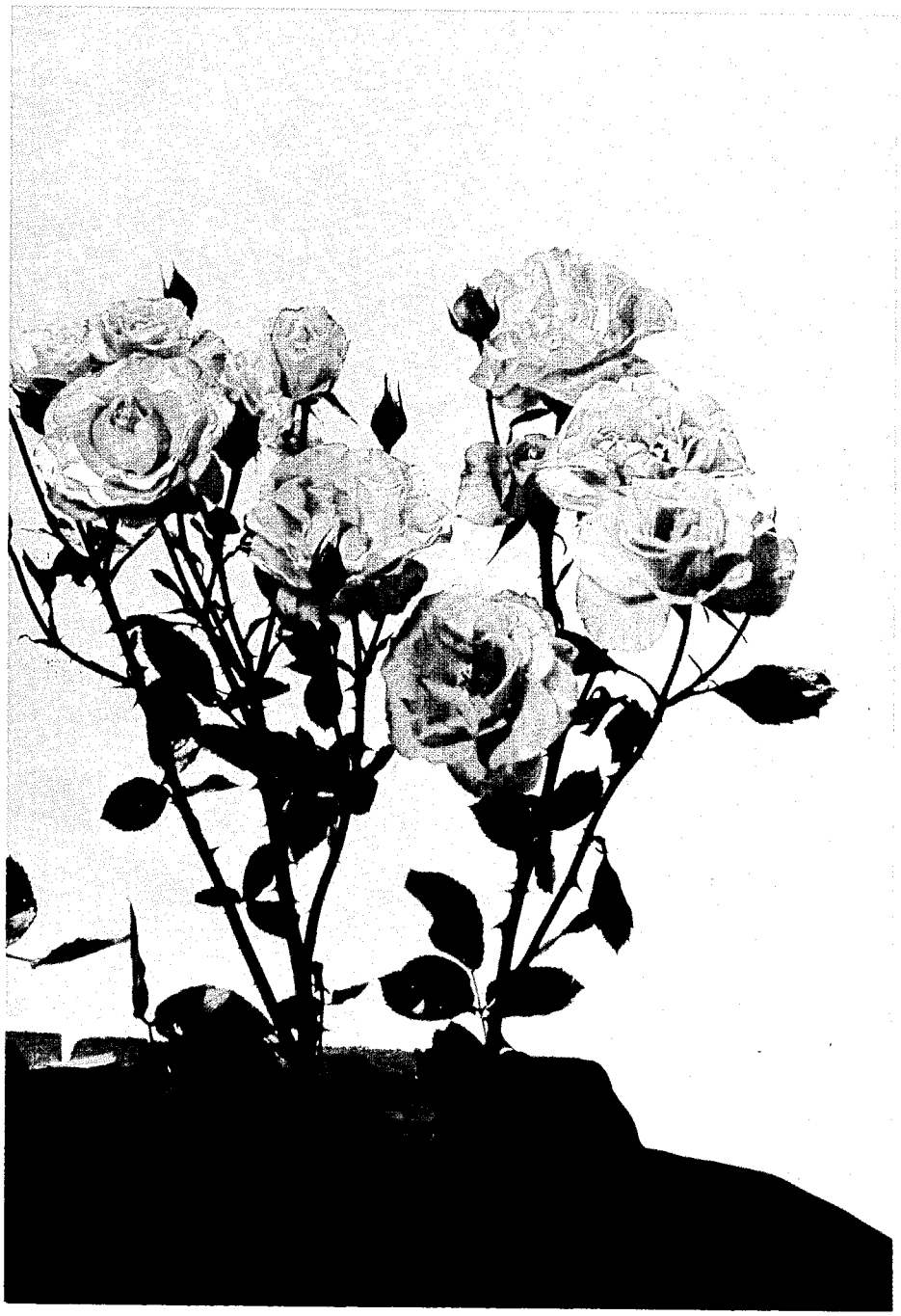

United States Patent Office

Plant Pat. 3,524
Patented Mar. 19, 1974

3,524

ROSE PLANT

Samuel McGredy, % S. McGredy & Sons,
Portadown, Northern Ireland

Filed Sept. 25, 1972, Ser. No. 291,574
Int. Cl. A01h 5/00
U.S. Cl. Plt.—22 1 Claim My new variety is primarily characterized by:

Plant low, somewhat spreading, 20–28 inches tall by 25–30 inches wide, sometimes 30 inches tall or more, sturdy and robust, full, compact, heavily branched, vigorous and very active even in hot weather. Stems sturdy yet graceful Sage Green and where exposed to direct sunlight when young tinted reddish brown to purple. Basal canes 20–25 in. long, the lateral branches up to 16 in. long, sometimes more on the heaviest canes. Internodes short, the third below the inflorescence usually 1¼ in. long or less. All canes and branches moderately to heavily armed with thorns and prickles except prickles may be lacking proximally. The thorns almost straight, slender, thin and very sharp, about ⅜ in. long with bases about ¼ in. long and 3/32 in. wide, light green with reddish bases when young, tan with brownish bases when mature. The prickles are borne throughout the plant except for the lowermost internodes of some canes and are especially dense on the peduncle.

The foliage dark green above, lighter below. The upper surface shiny Ivy Green (HCC 1060/3), the lower dull, slightly glaucous, Sage Green (HCC 861/1) lightly flushed Pansy Purple (HCC 928/3). The leaves 3–6 in. long by 2–2½ in. wide, three to seven leaflets with many seven leaflet leaves on the heavier canes. Terminal leaflets about 1½ to 2 in. long by 1–1¼ in. wide, finely biserrate, the teeth conspicuously apiculate. Rachis and midvein more heavily pigmented Pansy Purple than the blades.

The combination of the large abuandant foliage and the short internode length results in a plant that is so dense that the canes and branches are essentially hidden throughout much of their lengths.

Inflorescence cymose, flat, three to ten flowered, sometimes more.

The terminal flower opens 7–10 days ahead of the laterals and is borne conspicuously below the lateral buds in large clusters and even with or slightly exceeding the laterals in small 3–4 flowered inflorescences. The flowering laterals are produced along at least the upper half of each cane and in strong canes may arise almost from the base, making the plant's habit exceptionally full and compact. The peduncles are slender but strong, holding the flowers fully erect at all times, brownish green and densely covered with small prickles and glandular hairs.

Sepals lanceolate, slender, slightly ornate, apiculate, 1 3/16" long x 5/16" at base, Lavender Green (HCC 00076) above overlain Garnet Brown (HCC 00918/2). Reverse Parsley Green (HCC 00962/1) with glandular pubescence on reverse, the hairs dark contrasting with epidermis.

The receptical ordinary and hemispherical. The bud long and slender about 1⅛ in. long by ¾ in. wide of classical HT form, opening slowly to a high centered semi-double flower. The flowers large 2½–3¼ in. across, occasionally larger, high centered double with 12–15 petals and five to six petallaceous staminodes. Color of the petals Azalea Pink (HCC 618) to Claret Rose (HCC 021/1) overlain Carmine (HCC 21/1) to Currant Red (HCC 821/3) near the margins and in fresh flowers underlain straw Yellow (HCC 604) throughout resulting in a rich, orange color tone. Claw of petal Straw Yellow. Reverse of guard petals darker with red pigment more intense appearing nearly Blood Red (HCC 820/1). In all cases the reverse has more anthocyanin than the face. Color blend of fresh flowers results in true orange tones appearing Indian Orange (HCC 713/3) overlain Carmine near the edges.

Stamens about 110: anthers yellow, filaments darker, tinted light red proximally, light distally. Ovaries about 60, styles and stigmas light yellow.

The variety appears to be essentially sterile under conditions of culture at San Jose, Calif.

Asexual reproduction of my new variety by budding, through a series of propagations at Portadown, Northern Ireland, and San Jose, Calif., shows that all characteristic of the variety come true to form through succeeding propagations. The color references cited are those of the Horticultural Colour Charts of the Royal Horticultural Society. The parentage of my new Rose Plant is as follows: Parentage (Little Darling × Goldilocks) × Irish Mist.

I claim:

1. A new and distinct variety of rose of the Floribunda class primarily characterized by its dense, compact habit of growth with short internodes and profuse branching essentially hiding the canes from view; its tendency to produce flowering laterals one half to two thirds the length of the basal canes; its shiny, leathery, dark green, highly disease resistant large foliage which frequently carry seven leaflets, its perfectly spiralled petals of great substance which form its high centered, durable, semi-double flowers and by its color tones which range from soft Azalea Pink to rich Indian Orange which in turn mutate in aging from the more orange, darker color tones to the softer pink colors and which age and finish gracefully under all conditions and which clean before the petals spoil.

No references cited.

ROBERT E. BAGWILL, Primary Examiner